United States Patent [19]

Häbich et al.

[11] Patent Number: 4,849,531

[45] Date of Patent: Jul. 18, 1989

[54] PROCESS FOR THE PREPARATION OF 2,3-EPOXYAMIDES

[75] Inventors: Dieter Häbich; Wolfgang Hartwig, both of Wuppertal, Fed. Rep. of Germany

[73] Assignee: Bayer Aktiengesellschaft, Leverkusen, Fed. Rep. of Germany

[21] Appl. No.: 43,664

[22] Filed: Apr. 28, 1987

[30] Foreign Application Priority Data

May 7, 1986 [DE] Fed. Rep. of Germany ....... 3615520

[51] Int. Cl.$^4$ ............................................ C07D 301/24
[52] U.S. Cl. ..................................... 549/520; 549/521
[58] Field of Search ............................... 549/520, 521

[56] References Cited

U.S. PATENT DOCUMENTS 3,290,336 12/1966 McClure ............................. 549/520
4,577,036 3/1986 Falk ...................................... 549/556

FOREIGN PATENT DOCUMENTS 04588   11/1983 European Pat. Off. ........... 549/521
0126709 11/1984 European Pat. Off. .
0148128  7/1985 European Pat. Off. .
1144065  3/1969 United Kingdom ................ 549/521

OTHER PUBLICATIONS

Abstract of JA 73,577 (Apr. 1984).
The Chemical Society of Japan, Aug. 1984, 57, pp. 2135–2139.
Tetrahedron, vol. 40, No. 10, pp. 1795 to 1802, 1984.
J. Am. Chem. Soc. 1985, 107, pp. 1438–1439.
Tetrahedron Letters, vol. 26, No. 37, pp. 4521–4522, 1985.
Heterocycles, vol. 22, No. 8, 1984, pp. 1727–1728.
Pharmaceuticals–p. 5, Week 8518, J6–B.
Heterocycles, vol. 22, No. 8, 1984, pp. 1727–1728; Tetrahedron Letter vol. 26, No. 37, pp. 4521–4522, 1985.

*Primary Examiner*—Glennon H. Hollrah
*Assistant Examiner*—Amelia A. Owens

*Attorney, Agent, or Firm*—Sprung Horn Kramer & Woods

[57] ABSTRACT

A process for the preparation of a 2,3-epoxyamide of the formula

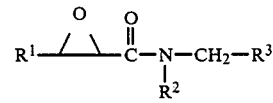

in which
$R^1$ represents hydrogen or straight-chain or branched $C_1$–$C_8$-alkyl, which may be substituted by phenyl or halogen, or represents $C_3$–$C_7$-cycloalkyl, phenyl, $C_1$–$C_8$-alkoxycarbonyl, or a group of the formula

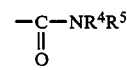

in which
$R^4$ and $R^5$ are identical or different and denote hydrogen, phenyl, benzyl, acetyl or $C_1$–$C_8$-alkyl which is optionally substituted by phenyl or halogen,
$R^2$ represents hydrogen or an amino protecting group and
$R^3$ represents a radical which activates the methylene group, comprising reacting a 2-halogeno-3-hydroxyamide of the formula

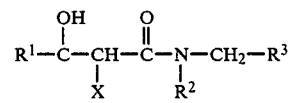

in which
X represents fluorine, chlorine, bromine or iodine,
with an alkali metal hydroxide in an inert solvent.

16 Claims, No Drawings

PROCESS FOR THE PREPARATION OF 2,3-EPOXYAMIDES

The invention relates to a new process for the preparation of 2,3-epoxyamides, some of which are known and which are important intermediates for the synthesis of carbapenem antibiotics.

It is known that appropriately substituted 2,3-epoxyamides are employed for the preparation of carbapenem antibiotics having hydroxyalkyl side chains in the 6 position [H. Maruyama et al., Tetrahedron Letters 1985, 4521; H. Shiozaki et al., Heterocycles 22, 1727 (1984)].

It is likewise known that such 2,3-epoxyamides are prepared from the appropriately substituted 2-halogeno-3-hydroxyamides by means of the action of strong bases. Alkali metal hydrides, alkali metal amides, bicyclic tertiary organic amines, alkyllithium compounds or other organolithium compounds were employed as bases here. These bases have several disadvantages. Thus, some of them are not readily available and must be prepared directly in the reaction solution. In addition, they are extremely air- and moisture-sensitive, so that their handling, and also the working up of relatively large batches, sometimes presents very high safety demands. The use of tertiary organic amines involves additional problems of difficult work-up, since 2,3-epoxyamides decompose under acid conditions.

A process for the preparation of 2,3-epoxyamides of the general formula (I)

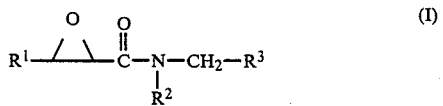

in which
R$^1$ represents hydrogen or straight-chain or branched C$_1$-C$_8$-alkyl, which may be substituted by phenyl or halogen, or represents C$_3$-C$_7$-cycloalkyl, phenyl, C$_1$-C$_8$-alkoxycarbonyl, or a group of the formula

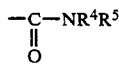

in which
R$^4$ and R$^5$ are identical or different and denote hydrogen, phenyl, benzyl, acetyl or C$_1$-C$_8$-alkyl which is optionally substituted by phenyl or halogen,
R$^2$ represents hydrogen or an amino protecting group and
R$^3$ represents a radical which activates the methylene group, has now been found that is characterized in that 2-halogeno-3-hydroxyamides of the general formula (II)

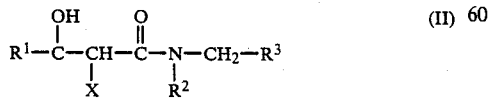

in which
R$^1$, R$^2$ and R$^3$ have the abovementioned meaning and X represents fluorine, chlorine, bromine or iodine, preferably bromine, are reacted with alkali metal hydroxides in inert solvents, either directly or in the presence of a phase transfer catalyst.

Surprisingly, the process according to the invention produces the desired 2,3-epoxyamides in good yields.

The process has the advantage that it can be carried out without great technical complexity. In the use, according to the invention, of alkali metal hydroxides as bases, there is no need to ensure absolute exclusion of water, since no combustible gases, such as hydrogen (when using hydrides as bases) or butane (when using butyllithium as base), can be produced. This allows the expense of special additional safety precautions to be avoided. In addition, the product can be obtained from the reaction mixture simply by filtration or extraction and subsequent evaporation of the solvent.

The 2,3-epoxyamides prepared by the processs according to the invention are generally defined by the formula (I).

When, in the context of the abovementioned definition, R$^2$ represents an amino protecting group, then it preferably represents a protecting group which is conventional in β-lactam chemistry, from the series comprising: 4-methoxyphenyl, 4-methoxymethyloxyphenyl, 4-[(2-methoxyethoxy)methyloxy]phenyl, 3,4-dimethoxyphenyl, benzyl, 2-nitrobenzyl, 4-nitrobenzyl, 4-methoxybenzyl, 2,4-dimethoxybenzyl, 3,4-dimethoxybenzyl, 2,4,6-trimethoxybenzyl, vinyl, allyl, tert-butoxycarbonyl, benzyloxycarbonyl, 2-nitrobenzyloxycarbonyl, 4-nitrobenzyloxycarbonyl, formyl, acetyl, chloroacetyl, trichloroacetyl, trifluoroacetyl, benzoyl, methoxycarbonyl, allyloxycarbonyl, 2,4-dimethoxybenzoyloxycarbonyl, 2,2-diethoxyethyl, methoxycarbonylmethyl, tert-butoxycarbonylmethyl, allyloxycarbonylmethyl, benzoylmethyl, bis-(4-methoxyphenyl)-methyl, methoxymethyl, methylthiomethyl, methoxyethoxymethyl, 2-(methylthiomethoxy)ethoxycarbonyl, 2-hydroxy-2-phenylmethyl, methoxy-(4-methoxyphenyl)-methyl, trimethylsilyl, triethylsilyl, triphenylsilyl, tert-butyl-dimethylsilyl, tert-butyl-diphenylsilyl and [2-(trimethylsilyl)ethoxy]-methyl.

If, in the context of the abovementioned definition, R$^2$ represents a radical which activates the methylene group, then it preferably represents an electron-drawing radical. These include, for example, ketone or ester groups, ether or thioether radicals, sulphinyl or sulphonyl groups, phosphonate groups, the nitrile or nitro group, or acetylene groups which are substituted by nitro, phenyl, ether, thioether, silyl, sulphonyl or ester groups.

2,3-Epoxyamides of the general formula (I) in which
R$^1$ represents hydrogen or straight-chain or branched C$_1$-C$_6$alkyl, which is optionally substituted by phenyl, fluorine, chlorine or bromine, or represents C$_3$-C$_6$-cycloalkyl, C$_1$-C$_6$-alkoxycarbonyl, or a group of the formula

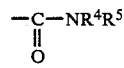

in which
R$^4$ and R$^5$ are identical or different and denote hydrogen or C$_1$-C$_6$-alkyl which is optionally substituted by phenyl, fluorine, chlorine or bromine,
R$^2$ represents hydrogen or an amino-protecting group from the series comprising 4-methoxyphenyl, 3,4-dimethoxyphenyl, 4-methoxymethyloxyphenyl, 4-[(2-methoxyethoxy)methyloxy]phenyl, benzyl, 4-methoxybenzyl, 2,4-dimethoxybenzyl, 3,4-dimethoxybenzyl, 2,4,6-trimethoxybenzyl, methoxy-(4-methoxyphenyl)methyl, trimethylsilyl, triethylsilyl, tert-butyldimethylsilyl, tert-butyldiphenylsilyl, vinyl, allyl, 2,2-diethoxyethyl, methoxycarbonylmethyl, tert-butoxycarbonylmethyl, benzoylmethyl or 2-hydroxy-2-phenylethyl and $R^3$ represents a group from the series comprising:

$-C{\equiv}C-C_6H_5$, $-C{\equiv}C-O-C_6H_5$, $-C{\equiv}C-S-C_6H_5$, $-C{\equiv}C-SO_2C_6H_5$, $-C{\equiv}C-NO_2$, $-C{\equiv}C-Si(CH_3)_3$, $-C{\equiv}C-COOCH_3$, $-C{\equiv}C-COOC_2H_5$, $-C{\equiv}C-COOC(CH_3)_3$, $-CN$, $-NO_2$, $-S-C_6H_5$, $-SO-C_6H_5$, $-SO_2-C_6H_5$, $-SO_2CH_3$, $-SO_2-C(CH_3)_3$, $-PO(OCH_3)_2$, $-PO(OC_2H_5)_2$, are preferably prepared by the process according to the invention.

2,3-Epoxyamides of the general formula (I) in which $R^1$ represents hydrogen, or straight-chain or branched $C_1$-$C_4$-alkyl which is optionally substituted by phenyl or by up to 3 fluorine atoms, or represents cyclopropyl, cyclopentyl, cyclohexyl, $C_1$-$C_4$-alkoxycarbonyl, or a group of the formula

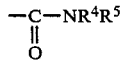

in which $R^4$ denotes hydrogen and $R^5$ denotes $C_1$-$C_4$-alkyl which is optionally substituted by phenyl, $R^2$ represents hydrogen, or an amino-protecting group from the series comprising 4-methoxyphenyl, 4-methoxybenzyl, 2,4-dimethoxybenzyl, 3,4-dimethoxybenzyl or tert-butyldimethylsilyl and $R^3$ represents a group from the series comprising:
—COOCH$_3$, —COOC$_2$H$_5$, —COOC(CH$_3$)$_3$,
—CO—C$_6$H$_5$, —SO$_2$—C$_6$H$_5$ or —SO$_2$—C(CH$_3$)$_3$, are particularly preferably prepared by the process according to the invention.

If (2S,3R)-N-(4-methoxyphenyl)-N-(tert-butoxycarbonylmethyl)-2-bromo-3-hydroxybutyramide is used as starting material, then the course of the reaction may be illustrated by the following equation:

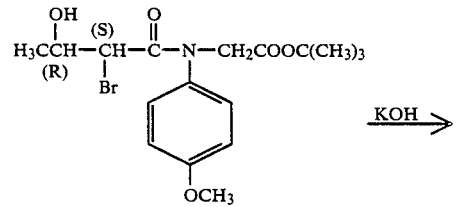

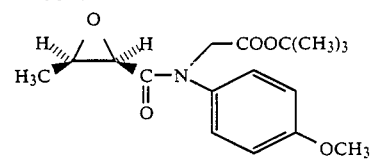

The 2-halogeno-3-hydroxyamides of the general formula (II) employed as starting materials are known or may be prepared by known methods [M. Shiozaki et al., Tetrahedron 40, 1795 (1984); M. Shiozaki et al., Heterocycles 22, 1727 (1984); H. Maruyama et al., Tetrahedron Lett. 1985, 4521; M. Shiozaki et al., Bull. Chem. Soc. Jpn., 57, 2135 (1984); European Patent Applications 148,128 and 126,709 and Japanese Patent Application 6,0051-171; Hanessian et al., J. Amer. Chem. Soc. 107, 1438 (1985)].

Suitable solvents are all inert organic solvents which do not change under the reaction conditions. These preferably include esters such as, for example, diethyl ether, dioxane, tetrahydrofuran, dimethoxyethane, diglyme, triglyme or tert-butyl methyl ether, or halogenated hydrocarbons such as, for example, methylene chloride, chloroform, carbon tetrachloride, dichloroethane, 1,1,2-trichloroethane, dichloroethylene, trichloroethylene, chlorobenzene or dichlorobenzene, or hydrocarbons such as benzene, toluene, xylene, hexane, cyclohexane or petroleum fractions, or ethyl acetate, acetonitrile, dimethylformamide, hexamethylphosphoric triamide, pyridine, picoline, morpholine or piperidine, or mixtures of the solvents mentioned.

Lithium hydroxide, potassium hydroxide or sodium hydroxide may preferably be employed as alkali metal hydroxides, potassium hydroxide or sodium hydroxide are particularly preferably used.

The alkali metal hydroxides used according to the invention may be employed in solid form, preferably powdered, or in the form of an aqueous solution, preferably an aqueous solution having a concentration of 10 to 60% by weight; preferably 30 to 55% by weight, of alkali metal hydroxide.

If the alkali metal hydroxide is employed according to the invention as a solid, then ethers such as diethyl ether, dioxane, tetrahydrofuran, dimethoxyethane or tert-butyl methyl ether, or hydrocarbons such as benzene, toluene, xylene or cyclohexane, or dimethylformamide, or mixtures of the solvents mentioned, are preferably employed as solvents.

If the alkali metal hydroxide is employed according to the invention in the form of an aqueous solution, it is preferably in the form of a 40 to 50% strength solution. In this case, halogenated hydrocarbons such as methylene chloride, carbon tetrachloride, 1,2-dichloroethane or 1,1,2-trichloroethane, or hydrocarbons such as benzene, toluene, xylene or cyclohexane, or mixtures of the solvents mentioned, are preferably employed as inert solvent.

The conventional phase transfer catalysts, such as quaternary arsonium, phosphonium, pyridinium, thiazolium or ammonium salts are employed, if appropriate, as phase transfer catalysts.

These preferably include: n-benzylcinchonidinium chloride, n-benzylcinchoninium chloride benzyldimethylhexadecylammonium chloride, benzyldimethyltetradecylammonium chloride, benzyltributylammonium bromide, benzyltributylammonium chloride, benzyltriethylammonium bromide, benzyltriethylammonium chloride, benzyltriethylammonium iodide, benzyltriethylammonium tetrafluoroborate, benzyltrimethylammonium bromide, benzyltrimethylammonium chloride, benzyltriphenylphosphonium bromide, diethylmethylpropylammonium bromide, (-)-N,N-dimethylephedrinium bromide, 3,4-dimethyl-5-(2-hydroxyethyl)-thiazolium iodide, dodecylethyldimethylammonium bromide, (-)-N-dodecyl-N-methylephedrinium bromide, ethyldimethylpropylammonium bromide, ethylhexadecyldimethylammonium bromide, 3-ethyl-5-(2-hydroxyethyl)-4-methylthiazolium bromide, ethyltriphenylphosphonium bromide, hexadecylpyridinium bromide, hexadecylpyridinium chloride, hexadecyltributylphosphonium bromide, hexadecyltrimethylammonium bromide, hexadecyltrimethylammonium chloride, methyltrioctylammonium bromide, methyltrioctylammonium chloride, methyltrioctylammonium iodide, octadecyltrimethylammonium bromide, phenyltrimethylammonium bromide, phenyltrimethylammonium chloride, tetrabutylammonium bromide, tetrabutylammonium chloride, tetrabutylammonium hexafluorophosphate, tetrabutylammonium hydrogen sulphate, tetrabutylammonium hydroxide, tetrabutylammonium methanesulphonate, tetrabutylammonium perchlorate tetrabutylammonium tetrafluoroporate, tetrabutylammonium tetraphenylborate, tetrabutylammonium trifluoromethanesulphonate, tetrabutylphosphonium chloride, tetradecyltrimethylammonium bromide, tetradodecylammonium bromide, tetradodecylammonium perchlorate, tetraethylammonium bromide, tetraethylammonium chloride, tetraethylammonium hexafluorophosphate, tetraethylammonium hydroxide, tetraethylammonium perchlorate, tetraethylammonium tetrafluoroburate, tetraethylammonium trifluoromethanesulphonate, tetraheptylammonium bromide, tetrahexylammonium benzoate, tetrahexylammonium bromide, tetrahexylammonium chloride, tetrahexylammonium hydrogen sulphate, tetrahexylammonium iodide, tetrahexylammonium perchlorate, tetrakis-(decyl)-ammonium bromide, tetrakis-(decyl)-ammonium perchlorate, tetraoctylammonium bromide, tetraoctylammonium perchlorate, tetrapentylammonium bromide, tetrapentylammonium iodide, tetraphenylarsonium chloride, tetraphenylphosphonium bromide, tetraphenylphosphonium chloride, tetrapropylammonium bromide, tetrapropylammonium hydroxide, tetrapropylammonium iodide, tetrapropylammonium perchlorate, tetrapropylammonium tetrafluoroborate, tributylheptylammonium bromide tributylmethylammonium bromide, tributylmethylammonium chloride, tributylmethylammonium hydroxide, tributylmethylammonium iodide, tributylpentylammonium bromide, tricaprylmethylammonium chloride ("Aliquat 336"), triethylammonium bromide.

The following are particularly preferably employed as phase transfer catalysts: tetrabutylammonium chloride, tetrabutylammonium bromide, benzyltriethylammonium chloride, benzyltriethylammonium bromide, benzyltributylammonium chloride, benzyltributylammonium bromide, tricaprylmethylammonium chloride ("Aliquat 336").

The phase transfer catalysts may also be employed in the form of aqueous or alcoholic solutions. The phase transfer catalysts are preferably employed, according to the invention, when the alkali metal hydroxides are used in the form of their aqueous solution.

The phase transfer catalysts are generally employed in an amount from 0.01 to 25 mol%, preferably from 5 to 15 mol%. The alkali metal hydroxide may be employed in a large excess. In general, the alkali metal hydroxide is employed, according to the invention, in an amount from 1 mol to 200 mols, preferably from 1 mol to 100 mols, relative to 1 mol of starting compound.

The process according to the invention is generally carried out in a temperature range from $-20°$ C. to $+50°$ C., preferably from $0°$ C. to $+25°$ C.

The process according to the invention is generally carried out at atmospheric pressure, but it may also be carried out at superatmospheric or subatmospheric pressure.

EXAMPLE 1

(2R, 3R)-N-(tert-butoxycarbonylmethyl)-N-(4-methoxyphenyl)-2,3-epoxybutyramide

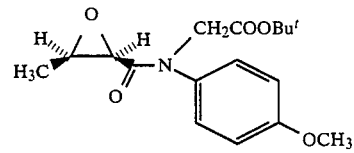

Process A 15.5 g (0.275 mol) of finely powdered potassium hydroxide were added to a solution of 100.6 g (0.25 mol) of (2R, 3R)-N-(4-methoxyphenyl)-N-(tert-butoxycarbonylmethyl)-2-bromo-3-hydroxybutyramide [M. Shiozaki et al., Tetrahedron 40, 1795 (1984)] in 1000 ml of tetrahydrofuran at room temperature, and the mixture was stirred for 5.5 hours at room temperature. When the reaction was complete, the potassium bromide produced was separated off by filtration and washed with tetrahydrofuran, and the filtrate solution was evaporated in vacuo. 77.1 g (96% of theory) of the title compound were obtained as an oil, $R_f = 0.24$ (toluene/ethyl acetate = 7:3).

IR (KBr) 1743, 1680, 1511, 1372, 1302, 1252, 1158 cm$^{-1}$.

$^1$H NMR (250 MHz, CDCl$_3$): $\delta = 1.44$ (d, J=6 Hz, CH$_3$CH); 1.48 (s, C(CH$_3$)$_3$) together 12H, 3.07 (dq, J=5 Hz, 6 Hz, 1H, H-3); 3.33 (d, J=6 Hz, 1H, H-2); 3.87 (s, 3H, OCH$_3$); 4.11 and 4.53 (AB, J=17.5 Hz, 2H, CH$_2$COO); 6.98 and 7.34 (AB, J=9.5 Hz, p-OCH$_3$-C$_6$H$_4$).

Process B 200 ml of a 50% strength (% by weight) solution of sodium hydroxide in water were added to a solution of 230.0 g (0.57 mol) of (2S, 3R)-N-(4-methoxyphenyl)-N-(tert-butoxycarbonylmethyl)-2-bromo-3-hydroxybutyramide in 1500 ml of dichloromethane, and the mixture was stirred intensively at room temperature for 15 minutes in the presence of 18.4 g (0.057 mol, 10 mol %) of tetrabutylammonium bromide. The organic phase was then separated off in a separating funnel, washed with 2 liters of water (3 x), 1 liter of 0.25N H$_2$SO$_4$ (1 x) and 1 liter of water (1 x), and dried over MgSO$_4$. After evaporation of the solvent in vacuo, 179.5 g (98% of theory) of the title compound were obtained as an oil, $R_f = 0.24$ (toluene:ethyl acetate = 7:3). The spectroscopic data were identical to the compound prepared by process A.

EXAMPLE 2

(2R)-N-(tert-butoxycarbonylmethyl)-N-(4-methoxyphenyl)-2,3-epoxypropionamide

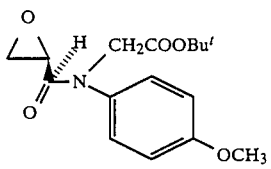

83.3 g (1.49 mols) of powdered potassium hydroxide were added at room temperature to a solution of 436.8 g (0.99 mol) of (2S)-N-(tert-butoxycarbonylmethyl)-N-(4-methoxyphenyl)-2-bromo-3-hydroxypropionamide in 3 liters of tetrahydrofuran, and the mixture was stirred for 3 hours at room temperature. After the reaction was complete, the potassium bromide produced was separated off by filtration and rinsed with tetrahydrofuran, and the filtrate solution was dried briefly over MgSO$_4$. After evaporation of the solvent in vacuo, 295.2 g (97% of theory) of the title compound was obtained as an oil, R$_f$=0.32 (toluene:ethyl acetate=7:3).

$^1$H NMR (300 MHz, CDCl$_3$): δ=1.45 (s, 9H, C(CH$_3$)$_3$); 2.74 (dd, J=7 Hz, 5 Hz, 1H, epoxide-H); 3.01 (dd, J=7 Hz, 3 Hz, 1H, epoxide-H); 3.25 (dd, J=5 Hz, 3 Hz, 1H, epoxide-H); 3.84 (s, 3H, OCH$_3$); 4.15 and 4.43 (AB, J=18 Hz, 2H, CH$_2$COO); 6.94 and 7.33 (AB, J=9 Hz, 4H, p-OCH$_3$-C$_6$H$_4$.

EXAMPLE 3

(2R, 3S)-N-(tert-butoxycarbonylmethyl)-N-(4-methoxyphenyl)-3-methoxycarbonyl-2,3-epoxypropionamide

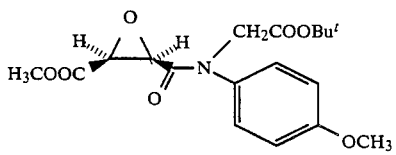

The title compound was obtained as colorless crystals, melting point: 90° C., R$_f$=0.17 (toluene:ethyl acetate=4:1), from 9.8 g (22 mmol) of (2S, 3R)-N-(tert-butoxycarbonylmethyl)-N-(4-methoxyphenyl)-2-bromo-3-hydroxy-3-methoxycarbonylpropionamide after 17 minutes at room temperature as described for process B from Example 1.

IR (CHCl$_3$) 1737 (C=O, ester), 1681 (C=O, amide) 1509 cm$^{-1}$.

$^1$H NMR (250 MHZ, CDCl$_3$): δ=1.44 (s, 9H, CH$_3$-C); 3.46 and 3.51 (AB, J=4.5 Hz, 2H, oxirane-H); 3.82 (s, 6H, OCH$_3$, COOCH$_3$); 4.08 and 4.36 (AB, J=16 Hz, CH$_2$COO); 6.91 and 7.31 (AB, J=9 Hz, 4H, p-OCH$_3$-C$_6$H$_4$).

EXAMPLE 4

(2R, 3R)-N-(benzoylmethyl)-N-(4-methoxyphenyl)-2,3-epoxybutyramide

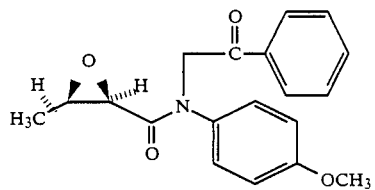

A procedure was carried out analogously to process B, Example 1. 50 g (0.123 mol) of (2S, 3R)-N-(4-methoxyphenyl)-N-(benzoylmethyl)-2-bromo-3-hydroxybutyramide [Hanessian et al., J. Am. Chem. Soc. 107, 1438 (1985)] were employed. 38.4 g (96% of theory) of the title compound having R$_f$=0.31 (cyclohexane:ethyl acetate=1:2) were obtained.

$^1$H NMR (250 MHz, CDCl$_3$): δ=1.48 (d, J=6 Hz, 3H, CH$_3$CH); 3.09 (dq, J=6 Hz, J=5 Hz, 1H, C(3)-H); 3.39 (d, J=5 Hz, 1H, C(2)-H); 3.82 (s, 3H, OCH$_3$); AB-signal (δ$_A$=4.87, δ$_B$=5.43, J$_{AB}$=16 Hz, 2H, CH$_2$-C=O); AB-signal (δ$_A$=6.92, δ$_B$=7.96, J=9 Hz, 4H, p-OCH$_3$-C$_6$H$_4$; 7.28–7.65 (m, 5H, C$_6$H$_5$).

EXAMPLE 5

(2R, 3R)-N-methoxycarbonylmethyl)-2,3-epoxybutyramide

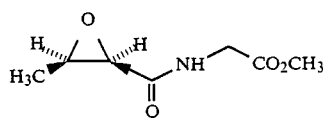

A procedure was carried out analogously to process B, Example 1. 25 g (0.098 mol) of (2S, 3R)-N-methoxycarbonylmethyl)-2-bromo-3-hydroxybutyramide were employed. 13.9 g (82% of theory) of the title compound having R$_f$=0.39 (ethyl acetate) were obtained.

$^1$H NMR (300 MHz, CDCl$_3$): δ=1.41 (d, J=6 Hz, 3 Hz, CH$_3$); 3.32 (dq, J=5 Hz, J=6 Hz, 1H, C(3)-H); 3.54 (d, J=5 Hz, 1H, C(2)-H); 3.78 (s, 3H, OCH$_3$); ABX-signal (δ$_A$=3.95, δ$_B$=4.23, J$_{AB}$=18.5 Hz, J$_{AM}$=J$_{BM}$=6 Hz, 2H, —CH$_2$—); 6.72 (br, 1H, NH).

EXAMPLE 6

(2R, 3R)-N-(methoxycarbonylmethyl)-N-(2,4-dimethoxyphenylmethyl)-2,3-epoxybutyramide

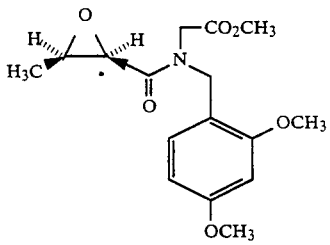

A procedure was carried out analogously to process B, Example 1. 50 g (0.124 mol) of (2S, 3R)-N-methoxycarbonylmethyl)-N-(2,4-dimethoxyphenylmethyl)-2-bromo-3-hydroxybutyramide were employed. 38.8 g (97% of theory) of the title compound having R$_f$=0.25 (cyclohexane:ethyl acetate=1:2) were obtained.

$^1$H NMR (250 MHz, CDCl$_3$): δ=1.40 (d, J=6 Hz, 3H, CH$_3$); 3.40 (d, q, J=5 Hz, J06 Hz, 1H, C(3)-H); 3.59

8d, J=5 Hz, 1H, C(2)-4); 3.73, 3.84, 3.86 (je, s, 9H, OCH₃); AB-signal ($\delta_A$=4.60 ($\delta_B$=4.58, J=17.5 Hz; 2H, CH₂CO₂); AB-signal ($\delta_A$=4.60, $\delta_B$=4.74, J=17 Hz, 2H, CH₂—C₆H₃OCH₃)₂); AB-signal ($\delta_A$=6.47, $\delta_B$=7.10, J=9 Hz, 2H, C(5), C(6)-C₆H₃(OCH₃)₂); 6.51 (s, 1H, C(3)-C₆H₃(OCH₃)₂).

It is understood that the specification and examples are illustrative but not limitative of the present invention and that other embodiments within the spirit and scope of the invention will suggest themselves to those skilled in the art.

We claim:

1. A process for the preparation of a 2,3-epoxyamide of the formula

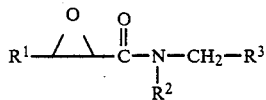

in which
R¹ represents hydrogen or straight-chain or branched C₁₋₈alkyl, which may be substituted by phenyl or halogen, or represents C₃₋₇-cycloalkyl, phenyl, C₁₋₈alkoxycarbonyl, or a group of the formula

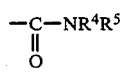

in which
R⁴ and R⁵ are identical or different and represent hydrogen, phenyl, acetyl or C₁₋₈-alkyl which is optionally substituted by phenyl or halogen,
R² represents hydrogen or an amino protecting group, and
R³ represents a member selected from the group consisting of

—C≡C—C₆H₅, —C≡C—O—C₆H₅, —C≡C—S—C₆H₅,

—C≡C—SO₂C₆H₅, —C≡C—NO₂, —C≡C—Si(CH₃)₃,

—C≡C—COOCH₃, —C≡C—COOC₂H₅,

—C≡C—COOC(CH₃)₃, —CN, —NO₂, —S—C₆H₅,

—SO—C₆H₅, —SO₂—C₆H₅, —SO₂CH₃, —SO₂—C(CH₃)₃,

—PO(OCH₃)₂, and —PO(OC₂H₅)₂, comprising reacting a 2-halogeno-3-hydroxyamide of the formula

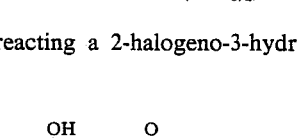

in which
X represents fluorine, chlorine, bromine or iodine, with an alkali metal hydroxide in an inert solvent.

2. A process according to claim 1, in which
R¹ represents hydrogen or straight-chain or branched C₁-C₆-alkyl, which is optionally substituted by phenyl, fluorine, chlorine, or bromine, or represents C₃-C₆-cycloalkyl, C₁-C₆-alkoxycarbonyl, or a group of the formula

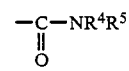

in which
R⁴ and R⁵ are identical or different and denote hydrogen or C₁-C₆-alkyl which is optionally substituted by phenyl, fluorine, chlorine or bromine,
R² represents hydrogen or an amino-protecting group from the group consisting of 4-methoxyphenyl, 3,4-dimethoxyphenyl, 4-methoxy-methoxyphenyl, 4-[(2-methoxyethoxy)-methoxy]phenyl, benzyl, 4-methoxybenzyl, 2,4-dimethoxybenzyl, 3,4-dimethoxybenzyl, 2,4,6-trimethoxybenzyl, methoxy-(4-methoxyphenyl)methyl, trimethylsilyl, triethylsilyl, tert-butyldimethylsilyl, tert-butyldiphenylsilyl, vinyl, allyl, 2,2-diethoxyethyl, methoxycarbonylmethyl, tert-butoxycarbonylmethyl, benzoylmethyl or 2-hydroxy-2-phenylethyl, and R³ represents

—C≡C—C₆H₅, —C≡C—O—C₆H₅, —C≡C—S—C₆H₅,

—C≡C—SO₂C₆H₅, —C≡C—NO₂, —C≡C—Si(CH₃)₃,

—C≡C—COOCH₃, —C≡C—COOC₂H₅,

—C≡C—COOC(CH₃)₃, —CH, —NO₂, —S—C₆H₅,

—SO—C₆H₅, —SO₂—C₆H₅, —SO₂CH₃, —SO₂—C(CH₃)₃,

—PO(OCH₃)₂, —PO(OC₂H₉)₂,

3. A process according to claim 1, in which
R¹ represents hydrogen or straight-chain or branched C₁-C₄-alkyl which is optionally substituted by phenyl or by up to 3 fluorine atoms, or represents cyclopropyl, cyclopentyl, cyclohexyl, C₁-C₄-alkoxycarbonyl, or a group of the formula

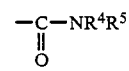

R⁴ denotes hydrogen wherein and
R⁵ denotes C₁-C₄-alkyl which is optionally substituted by phenyl,
R² represents hydrogen, or an amino-protecting group from the group consisting of 4-methoxyphenyl, 4-methoxybenzyl, 2,4-dimethoxybenzyl, 3,4-dimethoxybenzyl or tert-butyl-dimethylsilyl
R³ represents —COOCH₃, —COOC₂H₅, —COOC(CH₃)₃, —CO—C₆H₅, —SO₂—C₆H₅ or —SO₂—C(CH₃)₃.

4. A process according to claim 1, in which
R¹ is methyl,
R² is 4-methoxyphenyl, and
R³ is t-butoxycarbonylmethyl.

5. A process according to claim 1, in which
R¹ is methyl,
R² is 4-methoxyphenyl, and
R³ is benzoylmethyl.

6. A process according to claim 1, in which
R¹ is methyl,
R² is 2,4-dimethoxyphenyl, and R³ is methoxycarbonylmethyl.

7. A process according to claim 1, wherein the alkali metal hydroxide is lithium hydroxide, potassium hydroxide or sodium hydroxide and is employed in solid form or as an aqueous solution having a concentration of at least about 10% by weight.

8. A process according to claim 1, wherein the alkali metal hydroxide is lithium hydroxide, potassium hydroxide or sodium hydroxide and is employed in the form of an aqueous solution having a concentration of 10 to 60% by weight.

9. A process according to claim 1, wherein the alkali metal hydroxide is lithium hydroxide, potassium hydroxide or sodium hydroxide and is employed in the form of an aqueous solution having a concentration of 30 to 55% by weight.

10. A process according to claim 1, wherein the reaction is effected in the presence of about 0.01 to 25 mol % of a phase transfer catalyst based on the 2-halogeno-3-hydroxyamide.

11. A process according to claim 10, wherein the phase transfer catalyst is
n-benzylcinchonidinium chloride,
n-benzylcinchoninium chloride
benzyldimethylhexadecylammonium chloride,
benzyldimethyltetradecylammonium chloride,
benzyltributylammonium bromide,
benzyltributylammonium chloride,
benzyltriethylammonium bromide,
benzyltriethylammonium chloride,
benzyltriethylammonium iodide,
benzyltriethylammonium tetrafluoroborate,
benzyltrimethylammonium bromide,
benzyltrimethylammonium chloride,
benzyltriphenylphosphonium bromide,
diethylmethylpropylammonium bromide,
(-)-N,N-dimethylephedrinium bromide,
3,4-dimethyl-5-(2-hydroxyethyl)thiazolium iodide,
dodecylethyldimethylammonium bromide,
(-)-N-dodecyl-N-methylephedrinium bromide,
ethyldimethylpropylammonium bromide,
ethylhexadecyldimethylammonium bromide,
3-ethyl-5-(2-hydroxyethyl)-4-methylthiazolium bromide,
ethyltriphenylphosphonium bromide,
hexadecylpyridinium bromide,
hexadecylpyridinium chloride,
hexadecyltributylphosphonium bromide,
hexadecyltrimethylammonium bromide,
hexadecyltrimethylammonium chloride,
methyltrioctylammonium bromide,
methyltrioctylammonium chloride,
methyltrioctylammonium iodide,
octadecyltrimethylammonium bromide,
phenyltrimethylammonium bromide,
phenyltrimethylammonium chloride,
tetrabutylammonium bromide,
tetrabutylammonium chloride,
tetrabutylammonium hexafluorophosphate,
tetrabutylammonium hydrogen sulphate,
tetrabutylammonium hydroxide,
tetrabutylammonium methanesulphonate,
tetrabutylammonium perchlorate
tetrabutylammonium tetrafluoroporate,
tetrabutylammonium tetraphenylborate,
tetrabutylammonium trifluoromethanesulphonate,
tetrabutylphosphonium chloride,
tetradecyltrimethylammonium bromide,
tetradodecylammonium bromide,
tetradodecylammonium perchlorate,
tetraethylammonium bromide,
tetraethylammonium chloride,
tetraethylammonium hexafluorophosphate,
tetraethylammonium hydroxide,
tetraethylammonium perchlorate,
tetraethylammonium tetrafluoroburate,
tetraethylammonium trifluoromethanesulphonate,
tetraheptylammonium bromide,
tetrahexylammonium benzoate,
tetrahexylammonium bromide,
tetrahexylammonium chloride, or
tetrahexylammonium hydrogen sulphate.

12. A process according to claim 10, wherein the phase transfer catalyst is
tetrabutylammonium chloride,
tetrabutylammonium bromide,
benzyltriethylammonium chloride,
benzyltriethylammonium bromide,
benzyltributylammonium chloride,
benzyltributylammonium bromide or
tricaprylmethylammonium chloride ("Aliquat 336").

13. A process according to claim 1, wherein about 1 to 200 mols of the alkali metal hydroxide are present per mol of the 2-halogen-3-hydroxyamide.

14. A process according to claim 1, wherein the reaction is carried out at −20° C. to +25° C.

15. A process according to claim 1, wherein the reaction is carried out at 0° C. to +25° C.

16. A process according to claim 3, wherein the alkali metal hydroxide is lithium hydroxide, potassium hydroxide or sodium hydroxide and is employed in the form of an aqueous solution having a concentration of 30 to 55% by weight and the reaction is effected at 0° to 25° C. in the presence of about 0.01 to 25 mol % of a phase transfer catalyst based on the 2-halogeno-3-hydroxyamide, the phase transfer catalyst comprising
tetrabutylammonium chloride,
tetrabutylammonium bromide,
benzyltriethylammonium chloride,
benzyltriethylammonium bromide,
benzyltributylammonium chloride,
benzyltributylammonium bromide or
tricaprylmethylammonium chloride ("Aliquat 336"), about 1 to 200 mols of the alkali metal hydroxide being present per mol of the 2-halogeno-3-hydroxyamide.

* * * * *

UNITED STATES PATENT AND TRADEMARK OFFICE
CERTIFICATE OF CORRECTION

PATENT NO. : 4,849,531

DATED : July 18, 1989

INVENTOR(S) : Habich et al

It is certified that error appears in the above-identified patent and that said Letters Patent is hereby corrected as shown below:

Col. 6, line 32, Delete "2R," and substitute --2S,--.

Col. 9, line 26, Delete "$C_{1-8}$alkoxycarbonyl" and substitute --$C_{1-8}$-alkoxycarbonyl--.

Col. 10, line 47, Add new line 47 which is --wherein--.

Col. 10, line 48, After "hydrogen" delete "wherein".

Signed and Sealed this

Twenty-second Day of September, 1992

Attest:

DOUGLAS B. COMER

Attesting Officer

Acting Commissioner of Patents and Trademarks